(12) United States Patent
Maywald et al.

(10) Patent No.: US 8,716,487 B2
(45) Date of Patent: May 6, 2014

(54) PROCESS FOR PREPARING 4-HYDROXYPYRIDINES

(75) Inventors: Volker Maywald, Ludwigshafen (DE); Frederik Menges, Schriesheim (DE); Uwe Josef Vogelbacher, Ludwigshafen (DE); Michael Rack, Eppelheim (DE); Michael Keil, Freinsheim (DE); Wassilios Grammenos, Ludwigshafen (DE); Marianna Vrettou-Schultes, Mannheim (DE); Jan Klaas Lohmann, Lambsheim (DE); Bernd Mueller, Frankenthal (DE); Thorsten Jabs, Hassloch (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/805,567

(22) PCT Filed: Jun. 20, 2011

(86) PCT No.: PCT/IB2011/052681
§ 371 (c)(1), (2), (4) Date: Dec. 19, 2012

(87) PCT Pub. No.: WO2011/161612
PCT Pub. Date: Dec. 29, 2011

(65) Prior Publication Data
US 2013/0096312 A1 Apr. 18, 2013

Related U.S. Application Data

(60) Provisional application No. 61/357,128, filed on Jun. 22, 2010.

(30) Foreign Application Priority Data

Jun. 22, 2010 (EP) .................... 10166877

(51) Int. Cl.
*C07D 213/08* (2006.01)
*C07D 213/68* (2006.01)

(52) U.S. Cl.
CPC ........... *C07D 213/68* (2013.01); *C07D 213/08* (2013.01)
USPC ....................................... 546/303

(58) Field of Classification Search
CPC .......................... C07D 213/08; C07D 213/68
See application file for complete search history.

(56) References Cited

U.S. PATENT DOCUMENTS

2011/0105766 A1  5/2011  Smidt et al.

FOREIGN PATENT DOCUMENTS

| CN | 1560036 | 1/2005 |
| WO | WO 2008/074474 | 6/2008 |
| WO | WO 2009/156359 | 12/2009 |

OTHER PUBLICATIONS

Bobov, D. et al., Tetrahedron 2010, vol. 66, pp. 5432-5434.*
International Search Report dated Sep. 15, 2011, prepared in International Application No. PCT/IB2011/052681.
International Preliminary Report on Patentability dated Sep. 18, 2012, prepared in International Application No. PCT/IE32011/052681.
Bobrov, Denis N. et al., "Facile synthesis of caerulomycin E by the formation of 2,2'-bipyridine core via a 2-pyridyl substituted 4H-pyrran-4-one. Formal synthesis of caerulomycin A", Tetrahedron, 2010, p. 5432-5434, vol. 66.
Chandrasekhar, B., et al., "Development of an Efficient Process for 4,5, 6-Trichloroquinoline, A Key Intermediate for Agrochemical Synthesis", Organic Process Research & Development, 2002, p. 242-245, vol. 6.
Tyvorskii, Vladimir L., et al. "New Synthetic Approaches to 2-Perfluoroalkyl-4H-pyan-4-ones", Tetrahedron, 1998, p. 2819-2826, vol. 54.
Tyvorskii, V.I. et al., "New Method for the synthesis of 4-hydroxy-2-trifluoromethylpyridine", Chemistry of Hererocyclic Compounds, 1997, p. 995-996, vol. 33, No. 8.

* cited by examiner

*Primary Examiner* — Heidi Reese
(74) *Attorney, Agent, or Firm* — Brinks Gilson & Lione

(57) ABSTRACT

The present invention relates to a process for preparing 4-hydroxypyridines of formula I

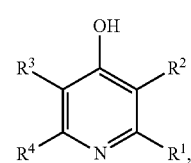

wherein $R^1$, $R^2$, $R^3$ and $R^4$ have the meanings defined in the description.

14 Claims, No Drawings

PROCESS FOR PREPARING 4-HYDROXYPYRIDINES

This application is a National Stage application of International Application No. PCT/IB2011/052681, filed Jun. 20, 2011, which claims the benefit of U.S. Provisional Application No. 61/357,128, filed Jun. 22, 2010, the entire contents of which are hereby incorporated herein by reference. This application also claims priority under 35 U.S.C. §119 to European Patent Application No. 10166877.0, filed Jun. 22, 2010, the entire contents of which is hereby incorporated herein by reference.

DESCRIPTION

The present invention relates to a process for preparing 4-hydroxypyridines.

Synthesis of substituted pyridines has been the subject of intensive investigations on account of their great versatility and their uses as components of active substances, especially of medicinal drugs and plant protection agents.

The reaction of an acetylacetone enol ether with ethyl perfluoroalkanoates in the presence of the strong base potassium tert-butoxide, followed by acid catalyzed cyclization to yield substituted pyranones has been disclosed by Tyvorskii et al. (Tetrahedron 54 (1998), 2819-2826). The preparation of 2-trifluoromethyl-4H-pyran-4-one by a similar synthesis has been disclosed by Tyvorskii et al. (Chem. Heterocycl. Comp. 33 (1997), 995). The pyranone was isolated and to a solution of the pyranone aqueous ammonia was added to obtain 4-hydroxy-2-trifluoromethylpyridine. The overall yield of the pyridine was only 40%×70%=28%.

WO 2008/074474 describes a multistep process for preparing O-modified 4-hydroxypyridine derivatives, that includes reacting 1,3-diketones with ammonia followed by N-acylation of the resulting α, β-unsaturated β-aminoketones with carboxylic acid halides or anhydrides and then ring formation by intramolecular aldol condensation giving substituted 4-hydroxypyridines in about 50 to 60% yield over 3 steps.

The present invention seeks to make available a synthesis for preparing substituted 4-hydroxypyridines that starts from readily available starting materials and that can be carried out very economically with high yields.

The invention relates to a process for preparing 4-hydroxypyridines of formula I

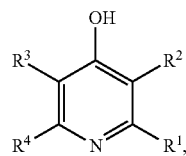

wherein $R^1$ is hydrogen, $C_1$-$C_4$-alkyl, $C_1$-$C_4$-haloalkyl, aryl, or hetaryl, where the two last-mentioned radicals are unsubstituted or substituted by substituents which are selected from halogen, $C_1$-$C_4$-alkyl, $C_1$-$C_4$-haloalkyl, $C_1$-$C_4$-alkoxy and $C_1$-$C_4$-haloalkoxy;

$R^2$, $R^3$ and $R^4$ independently are hydrogen, $C_1$-$C_4$-alkyl, $C_1$-$C_4$-haloalkyl, $NR^5R^6$ or aryl, where the aryl group is unsubstituted or substituted by 1, 2, 3 or 4 substituents which are selected from $C_1$-$C_4$-alkyl, $C_1$-$C_4$-haloalkyl, $C_1$-$C_4$-alkoxy and $C_1$-$C_4$-haloalkoxy;

or the radicals $R^3$ and $R^4$, together with the carbon atoms to which they are bound, form a 3-, 4-, 5-, 6- or 7-membered saturated, partly unsaturated or maximum unsaturated carbocyclic ring or a 3-, 4-, 5-, 6- or 7-membered saturated, partly unsaturated or maximum unsaturated heterocyclic ring containing 1, 2, or 3 heteroatoms selected from O, S and N as ring members, where the carbocyclic or heterocyclic ring is unsubstituted or substituted by 1, 2, 3 or 4 substituents selected from halogen, $C_1$-$C_4$-alkyl, $C_1$-$C_4$-haloalkyl, alkoxy and $C_1$-$C_4$-haloalkoxy;

$R^5$ is hydrogen, $C_1$-$C_4$-alkyl or $C_1$-$C_4$-haloalkyl;

$R^6$ is hydrogen, $C_1$-$C_4$-alkyl, $C_1$-$C_4$-haloalkyl, phenyl, and phenyl-$C_1$-$C_4$-alkyl; or $R^5$ and $R^6$ together form a linear $C_4$- or $C_5$-alkylene bridge or a group —$CH_2CH_2OCH_2CH_2$— or —$CH_2CH_2NR^7CH_2CH_2$—; and $R^7$ is hydrogen or $C_1$-$C_4$-alkyl;

the process comprising:

a) mixing a compound of formula II

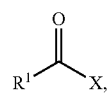

wherein $R^1$ is as defined above;
X is halogen or $C_1$-$C_4$-alkoxy;
with a compound of formula IIIa or IIIb

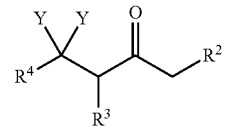

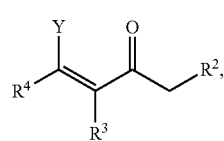

wherein $R^2$, $R^3$, $R^4$ are as defined above;
Y independently is halogen or $C_1$-$C_4$-alkoxy;
or the two radicals Y in a compound of formula IIIa together form a group —O—$(CH_2)_n$—O—, wherein the alkandiyl moiety —$(CH_2)_n$— is unsubstituted or substituted with 1, 2 or 3 substitutents selected from halogen and $C_1$-$C_4$-alkyl; and
n is 2, 3 or 4;
and at least one base selected from alkali metal methylates or alkali metal ethylates to form a reaction mixture;

b) after a first reaction period, the reaction mixture is treated with at least one acid; and c) after a second reaction period, the reaction mixture is treated with at least one ammonia source.

Unless otherwise defined, the general terms used herein have the following meanings:

The term "halogen" denotes fluorine, chlorine, bromine or iodine, especially fluorine, chlorine or bromine.

The term "$C_1$-$C_4$-alkyl" denotes a linear or branched alkyl radical comprising from 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term "$C_1$-$C_4$-haloalkyl" denotes straight-chain or branched alkyl groups having from 1 to 4 carbon atoms, where some or all of the hydrogen atoms of these groups have been replaced by halogen atoms. Examples thereof are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3,3,3-trifluoroprop-1-yl, 1,1,1-trifluoroprop-2-yl, 3,3,3-trichloroprop-1-yl, heptafluoroisopropyl, 1-chlorobutyl, 2-chlorobutyl, 3-chlorobutyl, 4-chlorobutyl, 1-fluorobutyl, 2-fluorobutyl, 3-fluorobutyl, 4-fluorobutyl and the like.

Likewise, The term "$C_1$-$C_4$-perhaloalkyl" denotes straight-chain or branched alkyl groups having from 1 to 4 carbon atoms, where all of the hydrogen atoms of these groups have been replaced by halogen atoms. Examples thereof are trifluoromethyl, trichloromethyl, pentafluoroethyl, heptafluoropropyl and the like.

The term "$C_1$-$C_4$-alkoxy" denotes straight-chain or branched saturated alkyl groups comprising from 1 to 4 carbon atoms, which are bonded via an oxygen atom. Examples of $C_1$-$C_4$-alkoxy are methoxy, ethoxy, n-propoxy, 1-methylethoxy (isopropoxy), n-butoxy, 1-methylpropoxy (sec-butoxy), 2-methylpropoxy (isobutoxy) and 1,1-dimethylethoxy (tert-butoxy).

The term "aryl" denotes carbocyclic aromatic radicals having from 6 to 14 carbon atoms. Examples thereof comprise phenyl, naphthyl, fluorenyl, azulenyl, anthracenyl and phenanthrenyl. Aryl is preferably phenyl or naphthyl, and especially phenyl.

The term "hetaryl" denotes aromatic radicals having from 1 to 4 heteroatoms which are selected from O, N and S. Examples thereof are 5- and 6-membered hetaryl radicals having 1, 2, 3 or 4 heteroatoms selected from O, S and N, such as pyrrolyl, furanyl, thienyl, pyrazolyl, imidazolyl, oxazolyl, isoxazolyl, thiazolyl, isothiazolyl, triazolyl, tetrazolyl, pyridyl, pyrazinyl, pyridazinyl, pyrimidyl and triazinyl.

The terms "compounds I", "compounds II", "compounds IIIa" and compounds "IIIb" refer to compounds of formulae I, II, IIIa and IIIb, respectively.

In the compounds I and II, $R^1$ is preferably hydrogen, $C_1$-$C_4$-alkyl, or $C_1$-$C_4$-haloalkyl. $R^1$ is more preferably $C_1$-$C_4$-perhaloalkyl, more preferably $C_1$-$C_2$-perhaloalkyl, e.g. trifluoromethyl or pentafluoroethyl, in particular trifluoromethyl.

In compounds I, IIIa and IIIb, $R^2$, $R^3$, $R^4$ are preferably hydrogen, $C_1$-$C_4$-alkyl or $C_1$-$C_4$-haloalkyl, in particular hydrogen.

In compounds II, X is preferably $C_1$-$C_4$-alkoxy, more preferably methoxy or ethoxy.

In compounds IIIa and IIIb, Y is preferably chlorine or $C_1$-$C_4$-alkoxy, more preferably $C_1$-$C_4$-alkoxy, in particular methoxy or ethoxy.

In compounds IIIa and IIIb, $R^3$ and $R^4$ preferably may also not form a carbo- or heterocyclic ring together with the carbon atoms to which they are attached; and more preferably may be, independently of each other, hydrogen, $C_1$-$C_4$-alkyl, $C_1$-$C_4$-haloalkyl, $NR^5R^6$ or aryl, where the aryl group is unsubstituted or substituted by 1, 2, 3 or 4 substituents which are selected from halogen, $C_1$-$C_4$-alkyl, $C_1$-$C_4$-haloalkyl, $C_1$-$C_4$-alkoxy and $C_1$-$C_4$-haloalkoxy; wherein $R^5$ and $R^6$ are as defined above; or even more preferably $R^3$ and $R^4$ may be hydrogen or $C_1$-$C_4$ alkyl.

Particularly preferred embodiments relate to the preparation of compounds I, wherein compounds I carry one of the following combinations of the radicals $R^1$, $R^2$, $R^3$ and $R^4$ as defined in Table P below. These embodiments refer also to the definition of the same substituents in compounds II, IIIa and IIIb, where applicable.

TABLE P

| line | $R^1$ | $R^2$ | $R^3$ | $R^4$ |
|---|---|---|---|---|
| P-1 | H | H | H | H |
| P-2 | $CH_3$ | H | H | H |
| P-3 | $C_2H_5$ | H | H | H |
| P-4 | $C_3H_7$ | H | H | H |
| P-5 | $CClF_2$ | H | H | H |
| P-6 | $CCl_2F$ | H | H | H |
| P-7 | $CF_3$ | H | H | H |
| P-8 | $CHF_2$ | H | H | H |
| P-9 | $CH_2F$ | H | H | H |
| P-10 | $CF_2CH_3$ | H | H | H |
| P-11 | $CCl_2CH_3$ | H | H | H |
| P-12 | $CF_2CF_3$ | H | H | H |
| P-13 | $CCl_2CCl_3$ | H | H | H |
| P-14 | $CF_2CHF_2$ | H | H | H |
| P-15 | $CF_2CF_2CF_3$ | H | H | H |
| P-16 | $CCl_2CCl_2CCl_3$ | H | H | H |
| P-17 | $CF_2CF_2OCH_3$ | H | H | H |
| P-18 | H | $CH_3$ | H | H |
| P-19 | $CH_3$ | $CH_3$ | H | H |
| P-20 | $C_2H_5$ | $CH_3$ | H | H |
| P-21 | $C_3H_7$ | $CH_3$ | H | H |
| P-22 | $CClF_2$ | $CH_3$ | H | H |
| P-23 | $CCl_2F$ | $CH_3$ | H | H |
| P-24 | $CF_3$ | $CH_3$ | H | H |
| P-25 | $CHF_2$ | $CH_3$ | H | H |
| P-26 | $CH_2F$ | $CH_3$ | H | H |
| P-27 | $CF_2CH_3$ | $CH_3$ | H | H |
| P-28 | $CCl_2CH_3$ | $CH_3$ | H | H |
| P-29 | $CF_2CF_3$ | $CH_3$ | H | H |
| P-30 | $CCl_2CCl_3$ | $CH_3$ | H | H |
| P-31 | $CF_2CHF_2$ | $CH_3$ | H | H |
| P-32 | $CF_2CF_2CF_3$ | $CH_3$ | H | H |
| P-33 | $CCl_2CCl_2CCl_3$ | $CH_3$ | H | H |
| P-34 | $CF_2CF_2OCH_3$ | $CH_3$ | H | H |
| P-35 | H | H | $CH_3$ | H |
| P-36 | $CH_3$ | H | $CH_3$ | H |
| P-37 | $C_2H_5$ | H | $CH_3$ | H |
| P-38 | $C_3H_7$ | H | $CH_3$ | H |
| P-39 | $CClF_2$ | H | $CH_3$ | H |
| P-40 | $CCl_2F$ | H | $CH_3$ | H |
| P-41 | $CF_3$ | H | $CH_3$ | H |
| P-42 | $CHF_2$ | H | $CH_3$ | H |
| P-43 | $CH_2F$ | H | $CH_3$ | H |
| P-44 | $CF_2CH_3$ | H | $CH_3$ | H |
| P-45 | $CCl_2CH_3$ | H | $CH_3$ | H |
| P-46 | $CF_2CF_3$ | H | $CH_3$ | H |
| P-47 | $CCl_2CCl_3$ | H | $CH_3$ | H |
| P-48 | $CF_2CHF_2$ | H | $CH_3$ | H |
| P-49 | $CF_2CF_2CF_3$ | H | $CH_3$ | H |
| P-50 | $CCl_2CCl_2CCl_3$ | H | $CH_3$ | H |
| P-51 | $CF_2CF_2OCH_3$ | H | $CH_3$ | H |
| P-52 | H | H | H | $CH_3$ |
| P-53 | $CH_3$ | H | H | $CH_3$ |
| P-54 | $C_2H_5$ | H | H | $CH_3$ |
| P-55 | $C_3H_7$ | H | H | $CH_3$ |
| P-56 | $CClF_2$ | H | H | $CH_3$ |
| P-57 | $CCl_2F$ | H | H | $CH_3$ |
| P-58 | $CF_3$ | H | H | $CH_3$ |
| P-59 | $CHF_2$ | H | H | $CH_3$ |
| P-60 | $CH_2F$ | H | H | $CH_3$ |
| P-61 | $CF_2CH_3$ | H | H | $CH_3$ |
| P-62 | $CCl_2CH_3$ | H | H | $CH_3$ |
| P-63 | $CF_2CF_3$ | H | H | $CH_3$ |
| P-64 | $CCl_2CCl_3$ | H | H | $CH_3$ |
| P-65 | $CF_2CHF_2$ | H | H | $CH_3$ |

TABLE P-continued

| line | R$^1$ | R$^2$ | R$^3$ | R$^4$ |
|---|---|---|---|---|
| P-66 | CF$_2$CF$_2$CF$_3$ | H | H | CH$_3$ |
| P-67 | CCl$_2$CCl$_2$CCl$_3$ | H | H | CH$_3$ |
| P-68 | CF$_2$CF$_2$OCH$_3$ | H | H | CH$_3$ |
| P-69 | H | H | H | CH$_3$ |
| P-70 | CH$_3$ | H | H | CH$_3$ |
| P-71 | C$_2$H$_5$ | H | H | CH$_3$ |
| P-72 | C$_3$H$_7$ | H | H | CH$_3$ |
| P-73 | CClF$_2$ | H | H | CH$_3$ |
| P-74 | CCl$_2$F | H | H | CH$_3$ |
| P-75 | CF$_3$ | H | H | CH$_3$ |
| P-76 | CHF$_2$ | H | H | CH$_3$ |
| P-77 | CH$_2$F | H | H | CH$_3$ |
| P-78 | CF$_2$CH$_3$ | H | H | CH$_3$ |
| P-79 | CCl$_2$CH$_3$ | H | H | CH$_3$ |
| P-80 | CF$_2$CF$_3$ | H | H | CH$_3$ |
| P-81 | CCl$_2$CCl$_3$ | H | H | CH$_3$ |
| P-82 | CF$_2$CHF$_2$ | H | H | CH$_3$ |
| P-83 | CF$_2$CF$_2$CF$_3$ | H | H | CH$_3$ |
| P-84 | CCl$_2$CCl$_2$CCl$_3$ | H | H | CH$_3$ |
| P-85 | CF$_2$CF$_2$OCH$_3$ | H | H | CH$_3$ |
| P-86 | H | CF$_3$ | H | H |
| P-87 | CH$_3$ | CF$_3$ | H | H |
| P-88 | C$_2$H$_5$ | CF$_3$ | H | H |
| P-89 | C$_3$H$_7$ | CF$_3$ | H | H |
| P-90 | CClF$_2$ | CF$_3$ | H | H |
| P-91 | CCl$_2$F | CF$_3$ | H | H |
| P-92 | CF$_3$ | CF$_3$ | H | H |
| P-93 | CHF$_2$ | CF$_3$ | H | H |
| P-94 | CH$_2$F | CF$_3$ | H | H |
| P-95 | CF$_2$CH$_3$ | CF$_3$ | H | H |
| P-96 | CCl$_2$CH$_3$ | CF$_3$ | H | H |
| P-97 | CF$_2$CF$_3$ | CF$_3$ | H | H |
| P-98 | CCl$_2$CCl$_3$ | CF$_3$ | H | H |
| P-99 | CF$_2$CHF$_2$ | CF$_3$ | H | H |
| P-100 | CF$_2$CF$_2$CF$_3$ | CF$_3$ | H | H |
| P-101 | CCl$_2$CCl$_2$CCl$_3$ | CF$_3$ | H | H |
| P-102 | CF$_2$CF$_2$OCH$_3$ | CF$_3$ | H | H |
| P-103 | H | H | CF$_3$ | H |
| P-104 | CH$_3$ | H | CF$_3$ | H |
| P-105 | C$_2$H$_5$ | H | CF$_3$ | H |
| P-106 | C$_3$H$_7$ | H | CF$_3$ | H |
| P-107 | CClF$_2$ | H | CF$_3$ | H |
| P-108 | CCl$_2$F | H | CF$_3$ | H |
| P-109 | CF$_3$ | H | CF$_3$ | H |
| P-110 | CHF$_2$ | H | CF$_3$ | H |
| P-111 | CH$_2$F | H | CF$_3$ | H |
| P-112 | CF$_2$CH$_3$ | H | CF$_3$ | H |
| P-113 | CCl$_2$CH$_3$ | H | CF$_3$ | H |
| P-114 | CF$_2$CF$_3$ | H | CF$_3$ | H |
| P-115 | CCl$_2$CCl$_3$ | H | CF$_3$ | H |
| P-116 | CF$_2$CHF$_2$ | H | CF$_3$ | H |
| P-117 | CF$_2$CF$_2$CF$_3$ | H | CF$_3$ | H |
| P-118 | CCl$_2$CCl$_2$CCl$_3$ | H | CF$_3$ | H |
| P-119 | CF$_2$CF$_2$OCH$_3$ | H | CF$_3$ | H |
| P-120 | H | H | H | CF$_3$ |
| P-121 | CH$_3$ | H | H | CF$_3$ |
| P-122 | C$_2$H$_5$ | H | H | CF$_3$ |
| P-123 | C$_3$H$_7$ | H | H | CF$_3$ |
| P-124 | CClF$_2$ | H | H | CF$_3$ |
| P-125 | CCl$_2$F | H | H | CF$_3$ |
| P-126 | CF$_3$ | H | H | CF$_3$ |
| P-127 | CHF$_2$ | H | H | CF$_3$ |
| P-128 | CH$_2$F | H | H | CF$_3$ |
| P-129 | CF$_2$CH$_3$ | H | H | CF$_3$ |
| P-130 | CCl$_2$CH$_3$ | H | H | CF$_3$ |
| P-131 | CF$_2$CF$_3$ | H | H | CF$_3$ |
| P-132 | CCl$_2$CCl$_3$ | H | H | CF$_3$ |
| P-133 | CF$_2$CHF$_2$ | H | H | CF$_3$ |
| P-134 | CF$_2$CF$_2$CF$_3$ | H | H | CF$_3$ |
| P-135 | CCl$_2$CCl$_2$CCl$_3$ | H | H | CF$_3$ |
| P-136 | CF$_2$CF$_2$OCH$_3$ | H | H | CF$_3$ |
| P-137 | H | H | H | CF$_3$ |
| P-138 | CH$_3$ | H | H | CF$_3$ |
| P-139 | C$_2$H$_5$ | H | H | CF$_3$ |
| P-140 | C$_3$H$_7$ | H | H | CF$_3$ |
| P-141 | CClF$_2$ | H | H | CF$_3$ |
| P-142 | CCl$_2$F | H | H | CF$_3$ |
| P-143 | CF$_3$ | H | H | CF$_3$ |
| P-144 | CHF$_2$ | H | H | CF$_3$ |
| P-145 | CH$_2$F | H | H | CF$_3$ |
| P-146 | CF$_2$CH$_3$ | H | H | CF$_3$ |
| P-147 | CCl$_2$CH$_3$ | H | H | CF$_3$ |
| P-148 | CF$_2$CF$_3$ | H | H | CF$_3$ |
| P-149 | CCl$_2$CCl$_3$ | H | H | CF$_3$ |
| P-150 | CF$_2$CHF$_2$ | H | H | CF$_3$ |
| P-151 | CF$_2$CF$_2$CF$_3$ | H | H | CF$_3$ |
| P-152 | CCl$_2$CCl$_2$CCl$_3$ | H | H | CF$_3$ |
| P-153 | CF$_2$CF$_2$OCH$_3$ | H | H | CF$_3$ |

The reactions described herein are carried out in reaction vessels customary for such reactions, such as a stirred reactor. In addition, the reaction is configurable not only in a batchwise manner but also in a continuous or semicontinuous manner. In general, the particular reactions will be performed under atmospheric pressure. However, the reactions can also be performed under reduced or elevated pressure.

In the process of the invention, steps a), b) and c) are preferably carried out without isolating any intermediate compound. More preferably, steps a), b) and c) are carried out in a single reaction vessel.

In step a) of the process of the invention, suitable bases are alkali metal methylates or alkali metal ethylates, e.g. lithium, sodium and potassium methylate and also lithium, sodium or potassium ethylate. Preferably, the base is sodium methylate or sodium ethylate, in particular sodium methylate. In another embodiment, the base is dissolved in a monohydric $C_1$-$C_4$-alcohol, preferably ethanol or methanol, even more preferably methanol. The base sodium methylate dissolved in methanol is particularly preferred. It is believed that alkali metal methylates have a suitable basicity to enable the reaction between the compound II and the compound IIIa or IIIb but also avoid unwanted side reactions and ensure the high yield of the desired product of formula I.

In step a) of the process of the invention, compounds II are preferably mixed with a compound IIIa.

In step a), the compound II, the compound IIIa or IIIb and the base can be contacted with one another in different sequences. However, it has generally been found to be advantageous to initially charge the compound II and the compound IIIa or IIIb, optionally dissolved and/or suspended in a solvent (mixture), and to add the base to the mixture of the compound II and the compound IIIa or IIIb.

The reaction in step a) can be carried out either in a solvent or in bulk. However, it has generally been found to be advantageous to use a solvent that serves to dissolve the base used. Preferably, a solution of the base in a suitable solvent is added to the mixture of the compound II and the compound IIIa or IIIb.

Suitable solvents depend on the selection of the base. Examples of useful organic solvents here include amides such as dimethylformamide or N-methylpyrrolidone, mono- or polyhydric alcohols such as monohydric $C_1$-$C_4$-alcohols, e.g. methanol, ethanol, n-propanol, isopropanol, n-butanol, s-butanol or tert-butanol, ethylene glycol or trifluoroethanol, or mixtures of these organic solvents with one another. Monohydric $C_1$-$C_4$-alcohols are more preferred, in particular methanol.

In an embodiment, the solvents are used in degassed form (i.e. especially freed of oxygen). The degassing of solvents is known and can be effected, for example, by single or multiple freezing of the solvent, thawing under reduced pressure (to remove the gas dissolved/dispersed in the solvent) and compensating with an inert gas, such as nitrogen or argon. Alternatively or additionally, the solvent can be treated with ultrasound.

Compounds II are commercially available or obtainable via standard organic synthetic methods. Methyltrifluoroacetate and ethyltrifluoroacetate are preferred examples of a compound II.

Compounds IIIa and IIIb are commercially available or obtainable via standard organic synthetic methods.

The relative amounts of compound II and of compound IIIa or IIIb can be subject to variation, but in practice, about equimolar amounts are used or a slight molar excess of the compound II is used. A molar ratio of the compound II, relative to the compound IIIa or IIIb, in the range of from 0.7 to 3.0 is generally suitable, with a molar ratio of from 1.0 to 2.0 being preferred.

An at least equimolar amount of the base is used, relative to the compound IIIa or IIIb; in practice, however, an excess is typically used. A molar ratio of the base, relative to compound IIIa or IIIb, in the range of from 1.0 to 3.0 is generally suitable, with a molar ratio of from 1.0 to 1.5 being preferred.

The reaction in step a) may be carried out in a wide temperature range, typically from −20° C. to 150° C. A practical temperature range is from 35 to 85° C. A preferred temperature range is from 40 to 70° C., for example about 60° C.

The first reaction period is not particularly limited and, typically, is in the range of from 10 minutes to 24 hours, preferably from 15 minutes to 1 hour. In general, the first reaction period is at least 30 seconds.

After the first reaction period, the reaction mixture is treated with at least one acid. In this step b), the reaction mixture and the acid can be contacted with one another in different sequences. However, it has generally been found to be advantageous to initially charge the acid, optionally dissolved in water, and to add the reaction mixture.

Acids are taken to mean Bronsted acids and their aqueous solutions. Preferred Bronsted acids are mineral acids, such as hydrohalic acids, sulfur acids, nitric acid, phosphorus acids, boric acid or oxy-halogen acids, in particular HCl, HBr, HI, HF, $H_2SO_4$, methanesulfonic acid, $KHSO_4$, $HNO_3$, $HClO_4$, $H_3PO_4$ and $H_3BO_3$ or nonhalogenated or halogenated $C_1$-$C_{22}$ alkanecarboxylic acids, i.e. unsubstituted or independently of one another substituted by up to 5 halogens such as F, Cl or Br, such as formic acid, acetic acid, trifluoroacetic acid, propionic acid, butyric acid, citric acid, oxalic acid, hexanoic acid, octanoic acid, decanoic acid (capric acid), dodecanoic acid (lauric acid), hexadecanoic acid (palmitic acid) or octadecanoic acid (stearic acid). Among these, preference is given to nonoxidizing acids.

Addition of an aqueous acid solution is generally preferred. In the case of the aqueous acid solutions, the amount of the Bronsted acid in the aqueous solution when use is made of mineral acids is preferably from 5 to 80% by weight, particularly preferably from 10 to 50% by weight.

HCl, $H_2SO_4$, formic acid and acetic acid are preferred due to their availability, HCl and $H_2SO_4$ being particularly preferred.

A molar amount of the acid is used that is in excess relative to the amount of base used in step a). A molar ratio of the acid, relative to the amount of base used in step a), in the range of from 1.5 to 4.0 is generally suitable, with a molar ratio of from 1.5 to 3.0 being preferred.

During the reaction in step b), the acid serves to cyclize the condensation product of compound II and compound IIIa or IIIb to form a 4-hydroxypyranone of formula IV

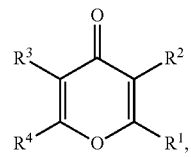

wherein $R^1$, $R^2$, $R^3$, and $R^4$ are as defined above.

In the process of the invention, the compound IV is converted in situ to a 4-hydroxypyridine compound I rather than being isolated.

The reaction in step b) may be carried out in a wide temperature range, typically from −20° C. to 150° C. A practical temperature range is from 35 to 85° C. A preferred temperature range is from 40 to 70° C., for example about 60° C.

The second reaction period is not particularly limited and, typically, is in the range of from 30 minutes to 24 hours, preferably from 1 hour to 5 hours. In preferred embodiments, the second reaction period is not longer than 2.5 hours.

After the second reaction period, the reaction mixture is treated with at least one ammonia source. In this step c), the reaction mixture and the ammonia source can be contacted with one another in different sequences. However, it has generally been found to be advantageous to initially charge the reaction mixture, and to add the ammonia source.

The ammonia source is suitably selected from ammonia, such as an aqueous ammonia solution or gaseous ammonia, ammonium halides, such as ammonium chloride or ammonium bromide, ammonium carboxylates, such as ammonium formate or ammonium acetate, and ammonium sulfate. Due to its ready availability, aqueous ammonia solution is preferred. The aqueous ammonia solution usually has a strength of 10 to 40% by weight. Alternatively, gaseous ammonia can be used as ammonia source. Gaseous ammonia is added to the reaction mixture either by passing it directly into the reaction mixture or by passing it into the gas phase above the reaction mixture.

According to embodiments, a solvent is added to the reaction mixture prior to the addition of the ammonia source. Among these embodiments preference is given to an embodiment, where after the first reaction period, an aqueous acid solution is added to the reaction mixture and prior to the addition of the ammonia source, a water immiscible solvent is added to the reaction mixture to form a biphasic reaction mixture.

Suitable water immiscible solvents include carboxylic esters, e.g. ethyl acetate, propyl acetate or ethyl propionate, open-chain ethers such as diethyl ether, dipropyl ether, dibutyl ether, methyl isobutyl ether and methyl tert-butyl ether (MTBE), aliphatic hydrocarbons such as pentane, hexane, heptane and octane, and petroleum ether, halogenated aliphatic hydrocarbons such as methylene chloride, trichloromethane, dichloroethane and trichloroethane, cycloaliphatic hydrocarbons such as cyclopentane and cyclohexane, and aromatic hydrocarbons such as toluene, the xylenes, chlorobenzene, dichlorobenzenes and mesitylene.

Such a biphasic solvent system may suitably also comprise at least one phase transfer catalyst. Suitable phase transfer catalysts are sufficiently well known to those skilled in the art and comprise, for example, charged systems such as organic ammonium salts, for example tetra($C_1$-$C_{18}$-alkyl)ammonium chlorides or bromides, such as tetramethylammonium chloride or bromide, tetrabutylammonium chloride or bromide, hexadecyltrimethylammonium chloride or bromide, octadecyltrimethylammonium chloride or bromide, methyltrihexylammonium chloride or bromide, methyltrioctylammonium chloride or bromide or benzyltrimethylammonium hydroxide (Triton B), and also tetra-($C_1$-$C_{18}$-alkyl)phosphonium chlorides or bromides such as tetraphenylphosphonium chloride or bromide, [(phenyl)$_m$—($C_1$-$C_{18}$-alkyl)$_n$]phosphonium chlorides or bromides in which m is from 1 to 3 and n is from 3 to 1 and the sum of m and n is 4, and also pyridinium salts such as methylpyridinium chloride or bromide, and uncharged systems such as crown ethers or aza crown ethers, for example 12-crown-4,15-crown-5, 18-crown-6, dibenzo-18-crown-6 or [2,2,2]-cryptand (222-Kryptofix), cyclodextrins, calixarenes such as [1$_4$]-metacyclophane, calix[4]arene and p-tert-butyl-calix[4]arene, and cyclophanes.

The reaction in step c) may be carried out in a wide temperature range, typically from −20° C. to 150° C. A practical temperature range is from 15 to 85° C. A preferred temperature range is from 20 to 70° C.

The reaction period after addition of the ammonia source is not particularly limited and, typically, is in the range of from 30 minutes to 24 hours, preferably from 1 hour to 5 hours.

The reaction mixture obtained is worked up and the compound I is isolated in a customary manner, for example by an aqueous, extractive workup, by removing the solvent, for example under reduced pressure, or by a combination of these measures. Further purification can be effected, for example, by crystallization, distillation or by chromatography.

The 4-hydroxypyridine compound I may be treated with a chlorinating agent to yield a 4-chloropyridine according to formula V

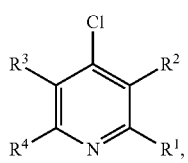

wherein $R^1$, $R^2$, $R^3$, and $R^4$ are as defined above.

Suitable chlorinating agents include inorganic or organic acid chlorides, such as, for example, phosphorus (III) chloride, phosphorus (V) chloride, phosphoryl chloride (phosphorus oxychloride), sulfuryl chloride, thionyl chloride and phosgene, with thionyl chloride and phosphoryl chloride being preferred.

Treatment with the chlorinating agent can be carried out either in bulk without addition of a diluent or in the presence of a suitable diluent. Suitable diluents include aliphatic, alicyclic or aromatic, optionally halogenated hydrocarbons, such as, for example, benzene, toluene, xylenes, chlorobenzene, dichlorobenzenes, petroleum ether, hexane, cyclohexane, methylcyclohexane, dichloromethane, chloroform, tetrachloromethane, and dimethylformamide (DMF), or their mixtures and in particular toluene and 1,2-dichlorobenzene.

Treatment with the chlorinating agent can optionally be carried out in the presence of a suitable reaction auxiliary. Those possible are tertiary amines, such as triethylamine, N,N-dimethylaniline, pyridine or 4-dimethylamino-pyridine, and also catalytic amounts of formamides, such as DMF or N,N-dibutylformamide, or metal halides such as magnesium chloride or lithium chloride.

In the treatment with the chlorinating agent, reaction temperatures can be varied within a relatively wide range. In general, the reaction is carried out at temperatures from 0° C. to 200° C., preferably from 10° C. to 180° C., in particular from 30° C. to 120° C.

The invention is illustrated by the following examples.

EXAMPLE 1

A methanol solution of sodium methylate (90 g, 30% by weight, 0.5 mol) was dissolved in 50 ml of N-methylpyrrolidone (NMP). 4-Methoxy-3-buten-2-one (10.2 g, 0.1 mol) and methyl perfluoro-propionate (21.4 g, 0.12 mol) were added dropwise and the mixture was strirred for further 48 hours at room temperature. Then, the reaction mixture was hydrolysed with water and the pH adjusted to 4 with hydrochloric acid (conc.). The product was extracted with methyl tert-butylether (MTBE), washed twice with water. After concentration of the organic phase, 19 g of the crude product containing 2-perfluoroethylpyran-4-one were obtained (HPLC purity 82%, yield: 73%).

EXAMPLE 2

A methanol solution of sodium methylate (16.2 g, 30% by weight, 0.09 mol) was dissolved in 50 ml of NMP. 4-Methoxy-3-buten-2-one (6.3 g, 0.06 mol) and methyl 2,2,3,3-tetrafluoroproprionate (12.09 g, 0.08 mol) were added dropwise and the mixture was strirred for further 48 hours at room temperature. Then, the reaction mixture was hydrolysed with water and the pH adjusted to 4 with hydrochloric acid (conc.). The product was extracted with MTBE, washed twice with water. After concentration of the organic phase, 6.3 g of the crude product containing 2-(2,2,3,3-tetrafluoroethyl)-pyran-4-one were obtained (HPLC purity 96%, yield: 51%).

EXAMPLE 3

A methanol solution of sodium methylate (11.3 g, 30% by weight, 0.06 mol) was dissolved in 50 ml of NMP. 4-Methoxy-3-buten-2-one (4.2 g, 0.04 mol) and ethyl 2,2-difluoroproprionate (7.0 g, 0.05 mol) were added dropwise and the mixture was strirred for further 48 hours at room temperature. Then, the reaction mixture was hydrolysed with water and the pH adjusted to 4 with hydrochloric acid (conc.). The product was extracted with MTBE, washed twice with water. After concentration of the organic phase, 4.0 g of the crude product containing 2-(2,2-difluoroethyl)-pyran-4-one were obtained (HPLC purity 92%, yield: 57%).

EXAMPLE 4

A methanol solution of sodium methylate (19.7 g, 30% by weight, 0.11 mol) was dissolved in 30 ml of NMP. 4-Methoxy-3-buten-2-one (2.2 g, 0.02 mol) and methyl 2,2,3,3-tetrafluoro-3-methoxy-proprionate (5.01 g, 0.03 mol) were added dropwise and the mixture was strirred for further 48 hours at room temperature. Then, the reaction mixture was hydrolysed with water and the pH adjusted to 4 with hydrochloric acid (conc.). The product was extracted with MTBE, washed twice with water. After concentration of the organic phase, 5.5 g of the crude product containing 2-(2,2,3,3-tetrafluoro-3-methoxy-ethyl)-pyran-4-one were obtained (HPLC purity 78%, yield: 95%).

EXAMPLE 5

A methanol solution of sodium methylate (36.9 g, 30% by weight, 0.2 mol) was dissolved in 150 ml of NMP. 4-Methoxy-3-buten-2-one (13.6 g, 0.14 mol) and ethyl perfluorobuyrate (39.5 g, 0.16 mol) were added dropwise and the mixture was strirred for further 48 hours at room temperature.

Then, the reaction mixture was hydrolysed with water and the pH adjusted to 4 with hydrochloric acid (conc.). The product was extracted with MTBE, washed twice with water. After concentration of the organic phase, 13 g of the crude product containing 2-perfluoropropylpyran-4-one were obtained (HPLC purity 93%, yield: 33%).

EXAMPLE 6

4,4-Dimethoxybutanone (20.0 g, 0.13 mol) and ethyl trifluoroacetate (28.7 g, 0.2 mol) were charged in a three neck flask. A methanol solution of sodium methylate (30% by weight, 38 ml, 0.2 mol) was added within 0.5 hours and the mixture was strirred for further 0.5 hours at 60° C. Then, hydrochloric acid (10% by weight, 146 ml, 0.400 mol) was added. The reaction mixture turned dark red. The reaction mixture was stirred for about 2.5 hours at 60 to 40° C.

Then aqueous ammonia (25% by weight, 45.3 ml, 0.67 mol) was added within 10 minutes at 40 to 50° C. and the mixture was stirred for about 18 hours at 50 to 22° C.

Methanol was removed from the reaction mixture by rotary evaporation. To the residue 200 g water and 200 g MTBE were added, and the mixture was stirred for 15 minutes. The organic phase was separated and the water phase was extracted with 50 g MTBE. The combined organic phases were evaporated to yield a dark oil (20.8 g) which contained 85.8% by weight of 4-hydroxy-2-trifluoromethylpyridine (yield: 82%).

EXAMPLE 7

4-Hydroxy-2-trifluoromethylpyridine (6.4 g, 39 mmol) was dissolved in 1,2-dichlorobenzene (64 g). Thionylchloride (23.2 g, 195 mmol) and DMF (10 drops) were added to the reaction mixture which was then heated to 70 to 80° C. After about 2 hours the reaction was completed and excess thionyl chloride was removed at an elevated temperature. The desired product was distilled under reduced pressure (50° C., 15 mbar) to yield 4-chloro-2-trifluoromethyl-pyridine (6.5 g, 36 mmol, yield: 92%). If required, remaining DMF was removed using an aqueous work-up.

The invention claimed is:

1. A process for preparing 4-hydroxypyridines of formula I

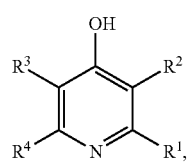

wherein
$R^1$ is hydrogen, $C_1$-$C_4$-alkyl, $C_1$-$C_4$-haloalkyl, aryl or hetaryl, where the two last-mentioned radicals are unsubstituted or substituted by 1, 2, 3 or 4 substituents which are selected from the group consisting of halogen, $C_1$-$C_4$-alkyl, $C_1$-$C_4$-haloalkyl, $C_1$-$C_4$-alkoxy, and $C_1$-$C_4$haloalkoxy;
$R^2$, $R^3$ and $R^4$ independently are hydrogen, $C_1$-$C_4$-alkyl, $C_1$-$C_4$-haloalkyl, $NR^5R^6$ or aryl, where the aryl is unsubstituted or substituted by 1, 2, 3 or 4 substituents which are selected from the group consisting of halogen, $C_1$-$C_4$-alkyl, $C_1$-$C_4$-haloalkyl, $C_1$-$C_4$-alkoxy and $C_1$-$C_4$-haloalkoxy;
or the radicals $R^3$ and $R^4$, together with the carbon atoms to which they are bound, form a 3-, 4-, 5-, 6- or 7-membered saturated, partly unsaturated or maximum unsaturated carbocyclic ring or a 3-, 4-, 5-, 6- or 7-membered saturated, partly unsaturated or fully unsaturated heterocyclic ring containing 1, 2, or 3 heteroatoms selected from the group consisting of O, S and N as ring members, where the carbocyclic or heterocyclic ring is unsubstituted or substituted by 1, 2, 3 or 4 substituents selected from the group consisting of halogen, $C_1$-$C_4$-alkyl, $C_1$-$C_4$-alkoxy and $C_1$-$C_4$-haloalkoxy;
$R^5$ is hydrogen, $C_1$-$C_4$-alkyl or $C_1$-$C_4$-haloalkyl;
$R^6$ is hydrogen, $C_1$-$C_4$-alkyl, $C_1$-$C_4$-haloalkyl, phenyl, or phenyl-$C_1$-$C_4$-alkyl;
or $R^5$ and $R^6$ together form a linear $C_4$- or $C_5$-alkylene bridge or a group —$CH_2CH_2OCH_2CH_2$— or —$CH_2CH_2NR^7CH_2CH_2$—; and
$R^7$ is hydrogen or $C_1$-$C_4$-alkyl;
the process comprising:
a) mixing a compound of formula II

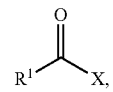

wherein $R^1$ is as defined above;
X is halogen or $C_1$-$C_4$-alkoxy;
with a compound of formula IIIa

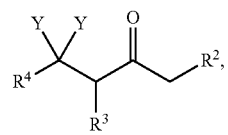

wherein $R^2$, $R^3$, $R^4$ are as defined above;
Y independently is halogen or $C_1$-$C_4$-alkoxy;
or the two radicals Y in a compound of formula IIIa together form a group —O—$(CH_2)_n$—O—, wherein the alkandiyl moiety —$(CH_2)_n$— is unsubstituted or substituted with 1, 2 or 3 substitutents selected from the group consisting of halogen and $C_1$-$C_4$-alkyl; and
n is 2, 3 or 4;
and at least one base selected from alkali metal methylates and alkali metal ethylates to form a reaction mixture;
b) after a first reaction period, the reaction mixture is treated with at least one acid; and
c) after a second reaction period, the reaction mixture is treated with at least one ammonia source.

2. The process as claimed in claim 1, wherein the base is selected from alkali metal methylates.

3. The process as claimed in claim 2, wherein the base is sodium methylate.

4. The process as claimed in claim 1, wherein the base is dissolved in a monohydric $C_1$-$C_4$-alcohol.

5. The process as claimed in claim 4, wherein the monohydric $C_1$-$C_4$-alcohol is methanol.

6. The process as claimed in claim 1, wherein in step a), b) and c) are carried out without isolating any intermediate compound.

7. The process as claimed in claim 1, wherein the acid is selected from mineral acids.

8. The process as claimed in claim 1, wherein the ammonia source is selected from the group consisting of aqueous ammonia solution, ammonium halides, ammonium carboxylates and ammonium sulfate.

9. The process as claimed in claim 1, wherein $R^1$ is hydrogen, $C_1$-$C_4$-alkyl or $C_1$-$C_4$-haloalkyl.

10. The process as claimed in claim 9, wherein $R^1$ is $C_1$-$C_4$-perhaloalkyl.

11. The process as claimed in claim 1, wherein $R^2$, $R^3$, $R^4$ are hydrogen, $C_1$-$C_4$-alkyl or $C_1$-$C_4$-haloalkyl.

12. The process as claimed in claim 11, wherein $R^2$, $R^3$, $R^4$ are hydrogen.

13. The process of claim 1, additionally comprising treating the compound I with a chlorinating agent to yield a 4-chloropyridine of formula V

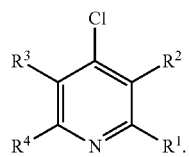

14. The process of claim 13, wherein the chlorinating agent is thionyl chloride or phosphoryl chloride.

* * * * *